United States Patent [19]

Vaguine et al.

[11] Patent Number: 4,556,070
[45] Date of Patent: Dec. 3, 1985

[54] HYPERTHERMIA APPLICATOR FOR TREATMENT WITH MICROWAVE ENERGY AND ULTRASONIC WAVE ENERGY

[75] Inventors: Victor A. Vaguine, Dallas, Tex.; Robert H. Giebeler, Jr., Cupertino; Albert H. McEuen, Saratoga, both of Calif.

[73] Assignee: Varian Associates, Inc., Palo Alto, Calif.

[21] Appl. No.: 547,307

[22] Filed: Oct. 31, 1983

[51] Int. Cl.$^4$ .............................................. A61N 1/00
[52] U.S. Cl. .................................................. 128/804
[58] Field of Search ............. 128/804, 24 A, 399–401, 128/783, 420–422, 800

[56] References Cited

U.S. PATENT DOCUMENTS

| | | | |
|---|---|---|---|
| 1,355,932 | 10/1920 | Walter | 128/401 |
| 2,232,156 | 2/1941 | Abeles | 128/399 |
| 2,283,285 | 5/1942 | Pohlman | 128/24 A |
| 2,415,352 | 2/1947 | Iams | 128/421 |
| 3,735,756 | 5/1973 | Richards et al. | 128/421 |
| 3,958,559 | 5/1976 | Glenn et al. | 128/660 |
| 3,971,962 | 6/1976 | Green | 128/660 |
| 3,973,235 | 8/1976 | van der Burgte | 128/660 |
| 4,119,102 | 10/1978 | LeVeen | 128/422 |
| 4,121,592 | 10/1978 | Whalley | 128/422 |
| 4,140,130 | 2/1979 | Storm, III | 128/422 |
| 4,315,514 | 2/1982 | Drewes et al. | 128/24 A |
| 4,397,314 | 8/1983 | Vaguine | 128/399 |
| 4,434,341 | 2/1984 | Busby | 128/804 |

OTHER PUBLICATIONS

I. Bahl et al., "New Microstrip Slot Radiator for Medical Applications", Electronic Letters, 9/11/80.
R. Greenwald et al., "A Computer Controlled System for Ultrasonic Hyperthermia Treatment" 8th Annual Northeast Bioengineering Conference, (1980).
M. Arslan, "Ultrasonic Selective Hypophysectomy" Ultrasonics, Apr. 1967.
D. A. Christensen et al., "Hyperthermia Production for Cancer Therapy: A Review of Fundamentals and Methods," *J. Microwave Power,* 16(2), 1981, p. 89.
W. Yang, "On Localized Hyperthermia by Electromagnetic and Ultrasonic Diathermy," ASME, Dec. 2–7, 1979.
P. P. Lele, "Induction of Deep, Local Hyperthermia by Ultrasound and Electromagnetic Fields," Radiat. Environ. Biophys. 17, 205–217, 1980.
D. A. Christensen, "A New Non-Perturbing Temperature Probe Using Semiconductor Band Edge Shift," *J. Bioengineering,* vol. 1, pp. 541–545, 1977.
A. Y. Cheung et al., "Direct Contact Applicators for Microwave Hyperthermia," *J. Microwave Power,* 16(2), 1981, p. 151.
V. A. Vaguine et al., "Microwave Direct-Contact Applicator System for Hyperthermia Therapy Research," Third Int. Symposium: Cancer Therapy by Hyperthermia, Drugs, and Radiation, Ft. Collins, Colorado, Jun. 1980.

*Primary Examiner*—Kyle L. Howell
*Assistant Examiner*—David Shay
*Attorney, Agent, or Firm*—Stanley Z. Cole; W. R. McClellan

[57] ABSTRACT

A direct contact hyperthermia applicator includes an ultrasonic lens with an array of ultrasonic transducers and an array of microwave antenna elements mounted behind the lens and positioned for transmission of ultrasonic wave energy and microwave energy therethrough. The antenna elements can be waveguide sections having radiating apertures or microstrip antenna elements. A fluid enclosure is defined between the front surface of the lens and a thin rubber sheet sealed around the periphery of the lens. During hyperthermia treatment, the rubber sheet conforms to the contours of the patient's body. The fluid, which is typically cooled distilled water, improves coupling of microwave energy and ultrasonic wave energy into the patient's body and cools the surface region.

8 Claims, 3 Drawing Figures

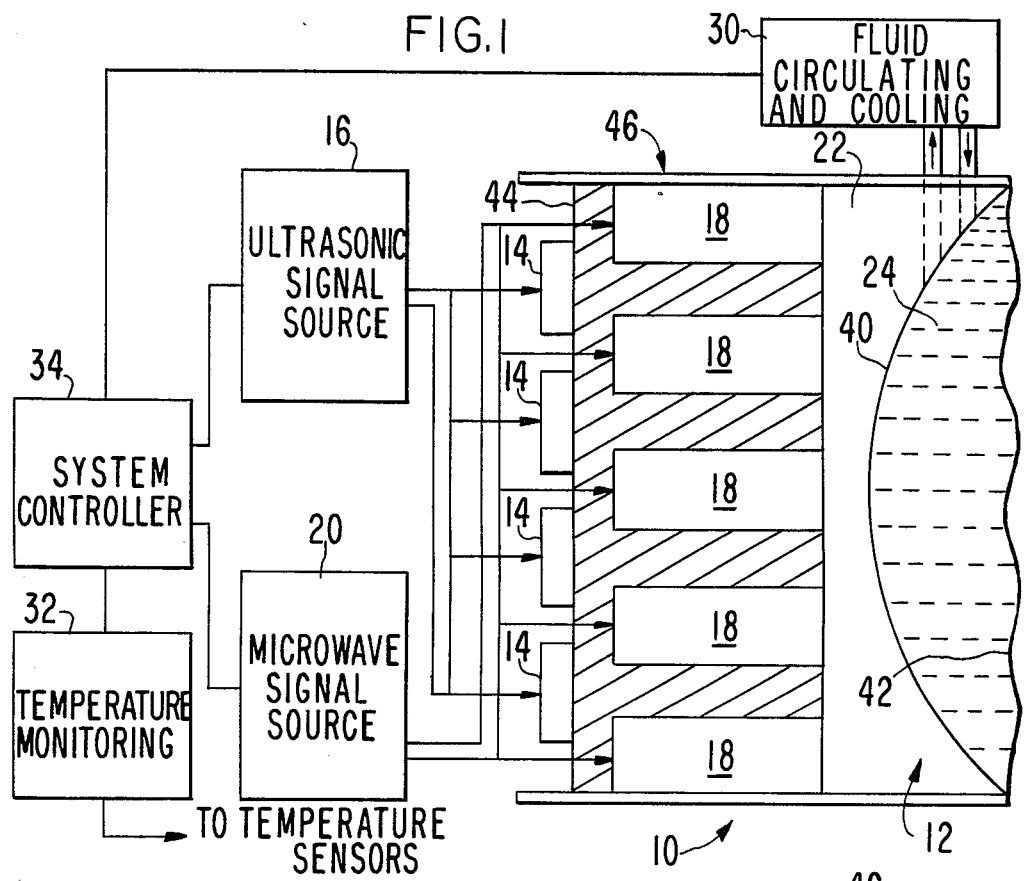
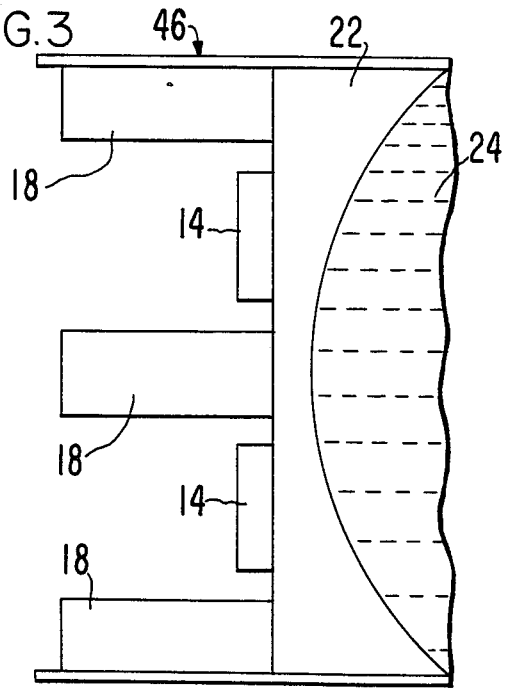
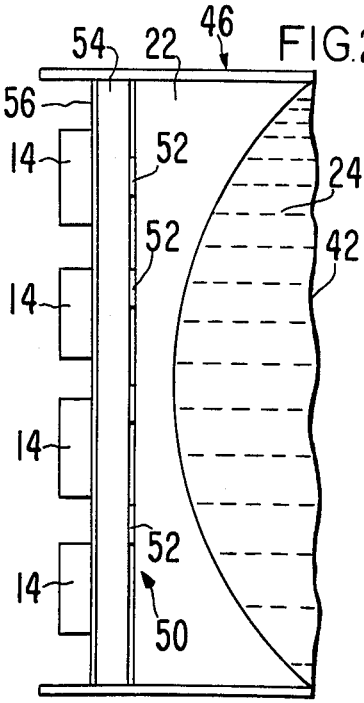

HYPERTHERMIA APPLICATOR FOR TREATMENT WITH MICROWAVE ENERGY AND ULTRASONIC WAVE ENERGY

BACKGROUND OF THE INVENTION

This invention relates to hyperthermia treatment of tissue by irradiation with microwave energy and ultrasonic wave energy and, more particularly, to applicators adapted for direct contact application of both microwave and ultrasonic wave energy.

Hyperthermia has received a great deal of attention in recent years as a form of cancer therapy. In hyperthermia, the temperature of a tumor is typically raised to the range of 42° C. to 45° C. Such temperatures can kill both malignant and normal cells. Hyperthermia is made practical by selective heating of tumors either alone or in conjunction with chemotherapy or radiation therapy. Microwave energy and ultrasonic wave energy have each been used to provide hyperthermia treatment. In either case, the malignant tissue must be heated to the desired temperature without overheating the surrounding normal tissue. External, or surface, applicators are preferable from a convenience standpoint.

In microwave hyperthermia, microwave energy has been applied to malignant tumors by various forms of applicators which act as antennas. The microwave energy is converted to heat in the tissue. Individual rectangular and circular waveguide sections having radiating apertures have been utilized for microwave hyperthermia treatment. However, individual microwave applicators have not been effective in heating deep-seated tumors. Frequencies above about 500 MHz are rapidly attenuated in tissue and do not produce substantial heating at depths beyond about 1 or 2 cm. Lower frequencies experience less attenuation in tissue but cannot be focused with practical sized applicators. Furthermore, measurement of the temperature rise caused by microwave treatment is difficult. When thermistors and thermocouples are used, measurement errors are caused by interactions between the connecting wires and the incident microwave fields. Nevertheless, microwave hyperthermia has proven more or less satisfactory in some cases (for example, when the tumor is located fairly close to or at the surface).

Ultrasonic wave energy is more effective than microwave energy in penetrating to deep-seated tumors and can be focused to a small volume with practical sized applicators. Also, since electromagnetic radiation is not used, temperature measurements can more easily be made. However, ultrasonic wave energy is reflected almost completely at an air/tissue interface and at a tissue/bone interface. Therefore, certain tumor locations are, to a great extent, inaccessible to ultrasonic hyperthermia treatment.

It has become evident to researchers that microwave hyperthermia treatment is more suitable in some situations and that ultrasonic hyperthermia treatment is more suitable in other situations. Furthermore, situations are encountered where simultaneous treatment with microwave energy and ultrasonic wave energy is required. It is desirable to provide hyperthermia applicators which can be utilized in all these situations.

It is a general object of the present invention to provide novel applicators for hyperthermia treatment of tissue.

It is another object of the present invention to provide applicators for hyperthermia treatment of tissue by irradiation with microwave energy and ultrasonic wave energy.

It is yet another object of the present invention to provide applicators for efficient hyperthermia treatment of tissue under a wide variety of circumstances.

SUMMARY OF THE INVENTION

According the present invention, these and other objects and advantages are achieved in an applicator for hyperthermia treatment of tissue by irradiation with microwave energy and ultrasonic wave energy. The applicator comprises ultrasonic wave focusing means fabricated from dielectric material having relatively low microwave attenuation and means for coupling microwave and ultrasonic wave energy between the focusing means and the tissue. The applicator further includes ultrasound transducer means positioned for transmission of ultrasonic wave energy through the focusing means and microwave antenna means positioned for transmission of microwave energy through the focusing means. The ultrasound transducer means is adapted for coupling to an ultrasonic signal source. The microwave antenna means is adapted for coupling to a microwave signal source. The ultrasound transducer means and the microwave antenna means can include arrays of ultrasound transducers and microwave antenna elements, respectively, and can be operated separately or simultaneously.

BRIEF DESCRIPTION OF THE DRAWINGS

For a better understanding of the present invention, together with other and further objects, advantages, and capabilities thereof, reference may be had to the accompanying drawings which are incorporated herein by reference and in which:

FIG. 1 shows a hyperthermia treatment system incorporating a hyperthermia applicator in accordance with the present invention;

FIG. 2 shows a cross-sectional view of another embodiment of the hyperthermia applicator in accordance with the present invention; and FIG. 3 shows a cross-sectional view of yet another embodiment of the hyperthermia applicator in accordance with the present invention.

DETAILED DESCRIPTION OF THE INVENTION

A hyperthermia treatment system incorporating the present invention is illustrated in FIG. 1. An applicator 10 is adapted to provide microwave energy and ultrasonic wave energy through an applicator output 12 to tissue under treatment. The applicator 10 includes a plurality of ultrasonic transducers 14 each coupled to an ultrasonic signal source 16. A plurality of microwave antenna elements 18, each coupled to a microwave signal source 20, is included in the applicator 10. The applicator 10 is provided with an ultrasonic wave lens 22 and, between the applicator output 12 and the lens 22, a fluid enclosure 24. The system can be provided with fluid circulation and cooling means 30 coupled to the enclosure 24. Hyperthermia treatment systems typically include one or more temperature sensors (not shown) coupled to a temperature monitoring means 32. The temperature sensors can be thermistors, thermocouples or, preferably, optical temperature sensors. Optical temperature sensors are described by D. A. Christiansen in "A New Non-Perturbing Temperature Probe Using Semiconductor Band Edge Shift," *J. Bioengineering,* Vol. 1, pp. 541-545, 1977. The sensors can be positioned on the skin and at various locations in or near the tumor under treatment. A system controller 34, in response to inputs from an operator, selects the radiation type, treatment times and temperatures, and monitors the operation of the system.

The ultrasonic signal source 16 supplies an electrical signal, typically in the frequency range between 300 KHz and 5 MHz, to each of the ultrasonic transducers 14 which are operative to convert the electrical energy to ultrasonic wave energy. The microwave source 20 supplies microwave power, typically in the frequency range between 400 MHz and 3,000 MHz, to each of the microwave antenna elements 18. The power outputs of each of the sources 16, 20 can be turned on and off and varied in level in response to control signals from the system controller 34. The fluid circulation and cooling means 30 can include a pump and a heat exchanger for circulating distilled cooled water through the enclosure 24. The circulation and cooling means 30 is controlled in its operation by the system controller 34. The temperature monitoring means 32 receives signals from the temperature sensors and supplies temperature information to the system controller 34. The temperature information can be displayed to the operator, can be recorded and can be used for control purposes to regulate the applied power and to automatically turn off the sources 16, 20 when a prescribed temperature is reached.

The ultrasonic wave lens 22 is a dielectric material, such as polystyrene, which is substantially transparent to both microwave energy and ultrasonic wave energy in the frequency ranges noted above. The lens 22 includes a flat rear surface and a concavely curved front surface. A flexible member 42, such as a thin sheet of rubber, is sealed fluid-tight around the periphery of the lens 22 to form the enclosure 24 which is filled with water. It will be understood that other liquids can be utilized. However, water has proven most convenient. Since the lens 22 and the water in the enclosure 24 have different ultrasonic wave propagation velocities, ultrasonic waves are refracted as they pass the front surface 40 of the lens 22. As is known, ultrasonic waves are reflected almost completely at an air/tissue interface. When the applicator 10 is placed on the skin of the patient, the flexible member 42 conforms to the surface contour of the patient's body in the region being treated, thereby eliminating any air/tissue interface. Similarly, the water in the enclosure 24 improves impedance matching between the applicator and the patient's body for microwave energy. In addition, by cooling the water circulated through the enclosure 24, surface heating caused either by the ultrasonic wave energy or by microwave energy is reduced.

The microwave antenna elements 18 are coupled to the rear surface of the ultrasonic wave lens 22 and, typically, include a radiating aperture at the output end. For example, the antenna elements 18 can be open-ended, rectangular waveguide sections. The use of individual rectangular waveguide sections is described generally by A. Y. Cheung et al in "Direct Contact Applicators For Microwave Hyperthermia," *J. Microwave Power,* 16(2), 1981, p. 151. Microwave power is coupled to the waveguide sections from a coaxial cable using known coupling techniques. The waveguide can be air filled or can be partially or completely filled with dielectric material to permit operation at lower frequencies. Alternatively, the antenna elements 18 can be dielectric loaded, cylindrical waveguides. See, for example, V. A. Vaguine et al, "Microwave Direct Contact Applicator System For Hyperthermia Therapy Research," Paper TE43, Third International Symposium: Cancer Therapy By Hyperthermia, Drugs and Radiation, Ft. Collins, Colorado, June 1980. In the applicator 10, the antenna elements 18 can be arranged in a two-dimensional array to provide a desired microwave radiation pattern. The excitation of each antenna element 18 can, if desired, be phase or amplitude controlled to produce a particular radiation pattern.

The antenna elements 18 are mounted in, or imbedded in, a block 44 of material which is substantially transparent to ultrasonic wave energy (for example, a metal). The block 44 is in contact with the rear surface of the ultrasonic wave lens 22. Mounted to the rear surface of the block 44 are the ultrasonic transducers 14. The construction of ultrasonic transducers is known generally in the art. Typically, electrical contacts are attached to opposite sides of a piezoelectric element. The piezoelectric element is mounted at its edges, such as by a cup shaped support, so that the central portion thereof is free to oscillate at the desired ultrasonic frequency. Impedance matching elements (not shown) may be required to match the impedance of the ultrasonic signal source 16 to the ultrasonic transducers 14. As shown in FIG. 1, the antenna elements 18 are spaced apart from each other, thereby providing paths through the block 44 between the transducers 14 and the lens 22 for transmission of ultrasonic wave energy. A small amount of the ultrasonic wave energy from the transducers 14 is transmitted through the antenna elements 18 to the lens 22.

A housing in the form of an outer shell 46 is provided for mounting and support of the above-described elements of the applicator 10. It will be understood that the configuration of the housing is optional.

In operation, the applicator 10 is positioned on the surface of the tissue, or body section, being treated so that the flexible member 42 is in direct contact with the surface and conforms to its shape. The temperature sensors are placed in desired locations to monitor the resultant heating. Depending on the size, shape and location of the tumor being treated, the hyperthermia treatment can include ultrasonic wave energy or microwave energy or both. As noted hereinabove, ultrasonic wave energy is more suitable for treatment of deep-seated tumors, while microwave energy is more suitable for treatment of tumors located near bones. One or both of the sources 16, 20 are energized and cooled water is circulated through the enclosure 24 under control of the system controller 34. During hyperthermia treatment, the temperature of the tissue is monitored by the temperature sensors. If a predetermined maximum temperature is exceeded, the power supplied by the sources 16, 20 can be reduced or shut off. The treatment is applied for a predetermined time, typically in the range of one half hour to one hour.

Another preferred embodiment of the applicator in accordance with the present invention is illustrated in FIG. 2. The applicator includes ultrasonic wave lens 22 and fluid enclosure 24, as described hereinabove in connection with FIG. 1. Attached to the rear surface of the lens 22 is a microstrip antenna 50. The microstrip antenna 50 comprises a dielectric layer 54 having a thin conductive layer 56 on its rear surface and one or more thin conductive antenna elements 52 on the surface facing the lens 22. The conductive layer 56 acts as a ground plane, while the antenna elements 52 radiate microwave energy in a prescribed pattern. The antenna elements 52 are formed by conventional photolithographic techniques. The dielectric layer 54 can be a material such as polystyrene, which is essentially transparent to ultrasonic wave energy. Mounted to the rear surface of the microstrip antenna 50 are ultrasonic transducers 14. Ultrasonic wave energy emitted by the transducers 14 passes through the microstrip antenna 50 and through the lens 22 with very little attenuation. Thus, microwave energy, ultrasonic wave energy or both can be provided by the applicator illustrated in FIG. 2.

Another embodiment of an applicator, in accordance with the present invention, is shown in FIG. 3. The applicator includes ultrasonic wave lens 22 and fluid enclosure 24, as described hereinabove in connection with FIG. 1. Ultrasonic transducers 14 are coupled directly to the rear surface of the lens 22 and transmit ultrasonic wave energy therethrough. Microwave antenna elements 18 are also coupled to the rear surface of the lens 22 and transmit microwave energy therethrough. The microwave antenna elements 18 are arranged in an array to provide a desired microwave radiation pattern. The ultrasonic transducers 14 are likewise arranged in an array, in the spaces between the elements 18, to provide a desired ultrasonic radiation pattern. The applicator shown in FIG. 3 is somewhat simpler in construction than the applicator 10 shown in FIG. 1 but makes less efficient use of the output aperture of the applicator for each radiation type.

While there has been shown and described what is at present considered the preferred embodiments of the invention, it will be obvious to those skilled in the art that various changes and modifications may be made therein without departing from the scope of the invention as defined by the appended claims.

We claim:

1. An applicator for hyperthermia treatment of tissue by irradiation with microwave energy and ultrasonic wave energy comprising:

ultrasonic wave focusing means fabricated from material having relatively low microwave attenuation;

means for coupling microwave and ultrasonic wave energy between said focusing means and said tissue;

an array of ultrasound transducers positioned for transmission of ultrasonic wave energy through said focusing means and adapted for coupling to a signal source;

an array of microwave antenna elements interspersed between said ultrasound transducers, positioned for transmission of microwave energy through said focusing means and adapted for coupling to a microwave signal source; and housing means for mounting the ultrasonic wave focusing means, the coupling means, the ultrasound transducers and the microwave antenna elements in fixed relative positions in a unitary assembly for hyperthermia treatment wherein the ultrasound transducers and the microwave antenna elements are positioned rearwardly of the focusing means such that ultrasonic wave energy and microwave energy with controlled radiation patterns and intensities can be transmitted through an output aperture of the assembly.

2. The applicator as defined in claim 1 wherein said microwave antenna elements comprise waveguide sections mounted at the rear surface of said focusing means, each of said waveguide sections including a radiating aperture.

3. The applicator as defined in claim 2 wherein said ultrasound transducers are positioned rearwardly of said antenna elements and ultrasonic wave energy is coupled to said focusing means through material interspersed between said antenna elements and having relatively low ultrasonic wave attenuation.

4. The applicator as defined in claim 3 wherein said means for coupling includes a fluid enclosure defined between the front surface of said focusing means and a flexible member sealed fluid-tight to said focusing means, said enclosure being filled with a fluid adapted for coupling microwave energy and ultrasonic wave energy between said focusing means and the tissue under treatment.

5. The applicator as defined in claim 4 further including means for circulating fluid through said enclosure for cooling the surface of said tissue.

6. The applicator as defined in claim 2 wherein said ultrasound transducers are mounted at the rear surface of said focusing means and positioned between said antenna elements.

7. An applicator for hyperthermia treatment of tissue by irradiation with microwave energy and ultrasonic wave energy comprising:

ultrasonic wave focusing means fabricated from material having relatively low microwave attenuation;

means for coupling microwave and ultrasonic wave energy between said focusing means and said tissue;

a microstrip antenna having a plurality of radiating elements mounted at the rear surface of the focusing means for transmission of microwave energy therethrough;

an array of ultrasound transducers mounted at the rear surface of the microstrip antenna so as to transmit ultrasonic wave energy through the microstrip antenna and the focusing means; and housing means for mounting the ultrasonic wave focusing means, the coupling means, the microstrip antenna and the ultrasound transducers in fixed relative positions in a unitary assembly for hyperthermia treatment wherein the ultrasound transducers and the microstrip antenna are positioned such that ultrasonic wave energy and microwave energy with controlled radiation patterns and intensities can be transmitted through an output aperture of the assembly.

8. The applicator as defined in claim 7 wherein said means for coupling includes a fluid enclosure defined between the front surface of said focusing means and a flexible member sealed fluid-tight to said focusing means, said enclosure being filled with a fluid adapted for coupling microwave energy and ultrasonic wave energy between said focusing means and the tissue under treatment.

* * * * *